(12) United States Patent
Yao et al.

(10) Patent No.: US 7,365,849 B2
(45) Date of Patent: *Apr. 29, 2008

(54) PORTABLE, SCANNING AND ANALYZING APPARATUS

(75) Inventors: Wen Fa Yao, Miaoli (TW); Chih Ming Wang, Miaoli (TW); Yung Chuan Liu, Miaoli (TW); Shih Yang Lo, Miaoli (TW); Roger Lai, Miaoli (TW); Kuang Pin Hsiung, Miaoli (TW)

(73) Assignee: Taiwan Unison Biotechnology, Inc., Miaoli (TW)

( * ) Notice: Subject to any disclaimer, the term of this patent is extended or adjusted under 35 U.S.C. 154(b) by 0 days.

This patent is subject to a terminal disclaimer.

(21) Appl. No.: 11/249,965

(22) Filed: Oct. 12, 2005

(65) Prior Publication Data
US 2006/0028648 A1    Feb. 9, 2006

Related U.S. Application Data

(63) Continuation-in-part of application No. 10/033,883, filed on Dec. 27, 2001, now Pat. No. 7,002,687.

(51) Int. Cl.
*G01J 3/46* (2006.01)
(52) U.S. Cl. ............................ 356/402; 356/409
(58) Field of Classification Search ................ 356/402, 356/408, 409
See application file for complete search history.

(56) References Cited

U.S. PATENT DOCUMENTS

| 4,317,137 A | * | 2/1982 | Tompkins | 358/472 |
|---|---|---|---|---|
| 4,430,299 A | * | 2/1984 | Horne | 422/64 |
| 4,554,460 A | * | 11/1985 | Klein | 250/208.2 |
| 4,871,258 A | * | 10/1989 | Herpichboehm et al. | 356/422 |
| 4,995,402 A | * | 2/1991 | Smith et al. | 600/584 |
| 5,112,134 A | * | 5/1992 | Chow et al. | 356/427 |
| 5,179,288 A | * | 1/1993 | Miffitt et al. | 250/564 |
| 5,216,597 A | * | 6/1993 | Beckers | 356/39 |
| 5,231,576 A | * | 7/1993 | Suzuki et al. | 356/39 |
| 5,281,395 A | * | 1/1994 | Markart et al. | 422/82.05 |
| 5,329,461 A | * | 7/1994 | Allen et al. | 702/26 |
| 5,349,172 A | * | 9/1994 | Roustaei | 235/462.42 |

(Continued)

FOREIGN PATENT DOCUMENTS

CN          1379245          11/2002

(Continued)

*Primary Examiner*—Roy M Punnoose
(74) *Attorney, Agent, or Firm*—J. C. Patents

(57) ABSTRACT

A portable, scanning and analyzing apparatus that uses an integrated scan probe for the scanning operation is described. The integrated scanning probe is formed with a light emitting diode array light source and a photodiode detector array. After a test sample finishes the reaction in test strip paper, a scanner device scans the test paper to collect the optical signals at variable, consecutive intervals along the scanning path to obtain the test signal accordingly. Then, the scanner device outputs the test signal for amplification. The amplified test signals are sent to an analog/digital converter such that the amplified test signals are converted into digital signals, which are then output to a computing unit for analyzing for subjective analytical results. The computing unit couples with the controller device, wherein the controller device controls a driver device that drives the scanner device to perform the scanning operation on the test paper.

15 Claims, 4 Drawing Sheets

U.S. PATENT DOCUMENTS

| | | | | |
|---|---|---|---|---|
| 5,730,124 A | * | 3/1998 | Yamauchi | 600/300 |
| 5,936,748 A | * | 8/1999 | Yamamoto | 358/504 |
| 6,043,880 A | * | 3/2000 | Andrews et al. | 356/311 |
| 6,071,249 A | * | 6/2000 | Cunningham et al. | 600/578 |
| 6,242,736 B1 | * | 6/2001 | Honma et al. | 250/306 |
| 6,372,184 B1 | * | 4/2002 | LaMoy et al. | 422/82.05 |
| 6,394,952 B1 | * | 5/2002 | Anderson et al. | 600/300 |
| 6,545,758 B1 | * | 4/2003 | Sandstrom | 356/317 |

FOREIGN PATENT DOCUMENTS

| | | |
|---|---|---|
| TW | 00164331 | 7/1991 |

\* cited by examiner

PORTABLE, SCANNING AND ANALYZING APPARATUS

CROSS-REFERENCE TO RELATED APPLICATION

This application is a continuation-in-part of a prior application Ser. No. 10/033,883, filed Dec. 27, 2001 now U.S. Pat. No. 7,002,687. All disclosures are incorporated herewith by reference.

BACKGROUND OF THE INVENTION

1. Field of the Invention

The invention relates to an analyzing apparatus. More particularly, the invention relates to a portable, scanning and analyzing apparatus.

2. Description of the Related Art

The advancement of technology provides medical devices with enhanced functionality. Currently, to properly diagnosis an illness, a blood sample or sample of other bodily fluids and excretions needs to be extracted from the patient by a medical practitioner for analysis. The patient needs to wait for at least few hours or even several days for the clinical results. Not only the treatment period is extended and the number of times for the hospital visit is increased, an undue deterioration of the illness may result due to a delayed intervention of the illness. For example, if a patent with a myocardial infarction condition is treated within several hours of the onset of the symptoms, the after-effect is minimized and the survival rate of the patent markedly increases. However, in reality, valuable time is already lost before the patient is being transported to the hospital. In addition, the time required for a sample extraction, the delivery of the sample for analysis and the actual sample analysis would further belated the proper medical treatment. As a result, the patient's life is greatly endangered.

On the other hand, along with the development of analytical techniques, test strip papers for urine analysis and immunoanalysis are broadly applied. Many test strip papers products are available for screening cancer markers, contagious diseases, narcotics, medications, cardiovascular diseases and veterinary applications. However, nowadays only a few 'quantitative' apparatus are available to read the test paper, the strip paper are visually determined by naked eyes. Still, only qualitative analysis is provided and quantitative analysis is not yet popular owing to the semi-quantitative nature, 'yet-bulky' size and high prices of the existing instrumentations appear onto the market in recent years. Since, the definition of 'quantitation' for the test results are mainly confined by the magnitude of imprecision measured at certain concentrations by the designated instrumentations. The larger the imprecision of the test results the larger the level of coefficient of variances. Therein, the criteria define the practical differences between 'semi-quantitation' and 'quantitation'. The down-size of the instrumentation is also crucial in the cases of performing on-site tests such as under the conditions of bed-site, ambulance, monitoring therapeutic drugs, narcotics, household tests and the tests in battlefield and veterinary field applications.

In summary, the current methods for clinical sample analysis has at least the following drawbacks. First of all, the time between the receiving of the patients' sample to making judgment and to the establishment of a confirmed analytical result is too long, the optimal time for treatment is thus delayed. Moreover, the current test papers can only produce a qualitative analysis result, and the result is subjectively determined. And the most of the point-of-care instrumentations in the market can only offer semi-quantitative results with insufficient reliability as reference for the therapeutic intervention during medical doctors' decision making. Still, the sizes of the instrumentations are not yet 'handy' to the field test applications on-site.

SUMMARY OF THE INVENTION

Accordingly, the present invention provides a portable, scanning and analyzing apparatus, wherein the apparatus is conformed with a scan probe optical unit configured integrally in an array. The entire apparatus is thus miniaturized to be easily portable. In a handheld prototype, the overall weight can construct to be no more than a couple of hundred grams. Not only a rapid screening for different situations can be provided, this type of apparatus allows the patient to timely receive the proper medical attention from the on-site screening, regardless of the whereabouts of the patients.

The present invention also provides a portable, scanning and analyzing apparatus, wherein the rapid on-site screening and the analyzing of the test result has been completed constitutively by a computing unit to allow for an accurate and subjective diagnosis.

The present invention further provides a portable, scanning and analyzing apparatus, wherein a test paper can be used in conjunction with the apparatus for a quantitative analysis. The test paper scan probe is driven by a step-in motor which pushes the system to scan across the test paper at a rate of 0.4 milli second per millimeter and collects optical signals at defined, consecutive intervals along the scanner device's scanning operation. Not only the screening process is unique and rapid, the simplicity in using the test strip paper can be fully exploited.

Therefore, in accordance to the present invention, a portable, scanning and analyzing apparatus is provided for any screening and testing operations conducted on an ambulance, bed-site, household, battlefield, farms or other emergency situations. Further, the test result is analyzed and the hospital is notified of the diagnosis. The preparation period before any medical treatment can be reduced to timely provide the appropriate therapeutic intervention. After a test sample is reacted with a test paper, a scanner device in the scanning and analyzing apparatus scans the test paper and a test signal is obtained accordingly. In order to attain sensitivity and reproducibility, optical signal is taken at every 0.04 millimeter across the defined area on test paper from the motor-driven scan probe consecutively. And all the optical signals thus taken are summing up to get the test signal. Further, during the scanning operation, the scanner device outputs the test signal to an amplifier. After the test signal is amplified, the signal is output to an analog/digital converter, and the digitized test signal is output to a computing unit for analysis to obtain an objective test result. Moreover, the computing unit is coupled to a controller device, wherein the controller device controls a driver device used in activating the scanner device to perform the scanning operation.

The present invention also utilizes a computing algorithm to minimize the noises to achieve background reduction especially when analyzing multi-analytes. It appears to be of great advantages in enhancing signal-to-noise ratio, S/N of multi-analytes test results from the proper handling of these optical signals to obtain low S/N test signals. Sensitivities and reproducibility can be further improved by repeatedly scanning of the test paper for test signals collection then averaged, to statistically reduce undetermined errors.

It is to be understood that both the foregoing general description and the following detaned description are exemplary, and are intended to provide further explanation of the invention as claimed.

BRIFE DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention and to show the practical applicability of the present invention.

Figure 3A:
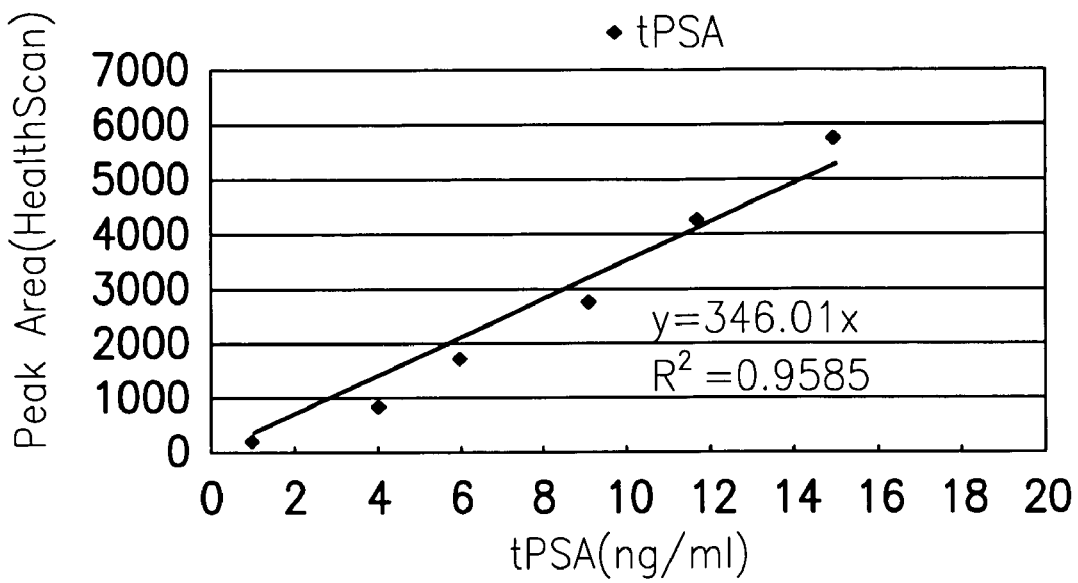
Figure 3B:
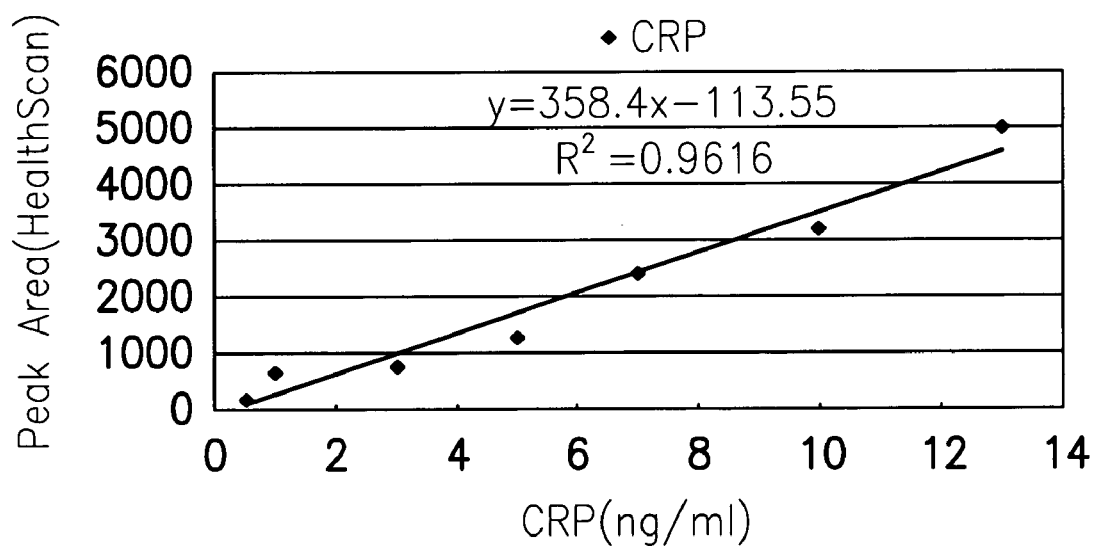

FIGS. 3a & b are the calibration curves of the diseases markers for prostate cancer screening i.e., prostate specific antigen-total and C-reactive protein, CRP, measured by portable, scanning and analyzing apparatus.

DESCRIPTION OF THE PREFERRED EMBODIMENTS

The portable, scanning and analyzing apparatus, designed according to the theory of the present invention, is adaptable to use on-site in point-of-care testing, POCT, various specific and emergency situations or daily self-monitoring due to its compact design and simplified operating procedure.

Table 1 summarizes the stability measurements over a four-months test running period for the portable, scanning and analyzing apparatus of the present invention.

TABLE 1

|         |      | 1'st month | 2'nd month | 3'rd month | 4'th month | Total |
|---------|------|------------|------------|------------|------------|-------|
| Level 1 | Mean | 133        | 130        | 128        | 128        | 130   |
|         | CV % | 0.4        | 2.7        | 2.8        | 1          | 2.5   |
| Level 2 | Mean | 82         | 80         | 78         | 76         | 79    |
|         | CV % | 0.7        | 2.1        | 4.4        | 2          | 3.3   |

Figure 1:
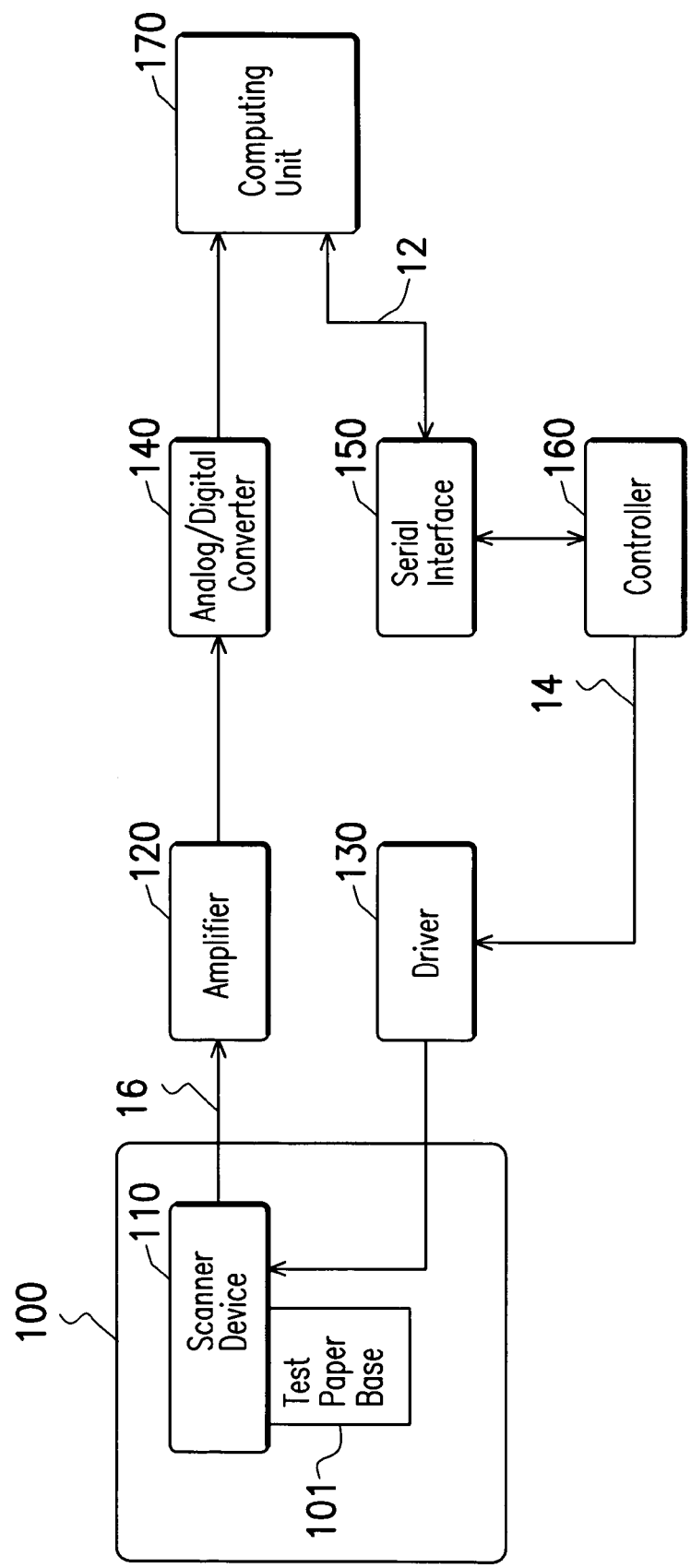
FIG. 1 is a block diagram schematically illustrates the different components of a portable, scanning and analyzing apparatus of the present invention.

In general, before the scanning and the analyzing are conducted, the sample (containing at least one or multiple analytes or substances to be tested) is placed on a test paper. The test paper is then inserted or delivered by other means into the scanning and analyzing apparatus comprising an optical unit. Thereafter, referring to FIG. 1, FIG. 1 is a block diagram schematically illustrates the different components of a portable, scanning and analyzing apparatus of the present invention. After the test sample reacts with the test paper, the test paper is delivered to a test paper base 101 in the scanning and analyzing apparatus 100 through a test paper tray or a test paper slot. A scanner device 110 consists of a scan probe, the optical unit and a step-in motor to scan the test paper and obtain a test signal 16 accordingly.

The scanning an analyzing apparatus 100, which is activated by a driver device 130, performs the scanning operation on the test paper and outputs the test signal 16 resulted from the scanning operation. When the scanning is conducted, the scanner device 110 of the scanning and analyzing apparatus 100 outputs the test signal to an amplifier 120. The test signal 16 is amplified and transmitted to an analog/digital converter 140. The test signal 16 converted into a digital test signal 16. The digital test signal 16 is further input to a computing unit 170 for analysis to attain an objective test result.

Meanwhile, the computing unit 170 can generate a control signal 12 via a reception of a command from a user or a triggering of certain meet conditions (for example, a signal of an inserted test paper). The computing unit 170 is also connected to a controller device 160 via a serial interface 150, wherein the serial interface 150 is configured between the computing unit 170 and controller device 160 transmits a driver signal 14 to the driver device 130 according to the control signal 12 to activate the scanner device 110 to conduct the scanning operation. The interface 150 can be, for example, an interface that satisfies the RS-232 standard or other devices with the similar function.

In order to provide a portable, scanning and analyzing apparatus, a battery can be designed as the power source to facilitate the locomotion of the device. Further other electrical charging mechanism can be applied during an emergency situation.

The scanner device 110 of the scanning and analyzing system of the present invention utilizes an integrated scan probe which includes a light emitting diode (LED) array light source and an optical fiber photodiode array detector. The light source of the scanning and analyzing apparatus of the instant case uses the LED array to provide a high light intensity. Further, there are red, yellow-green, blue and synthetic white light miniature LED array to be selected as light sources. Moreover, by complementing the antibody dyeing technique, of which the dyed-antibody is specific to the analyte with an appropriate selection of the light source, multi-analytes can be easily be performed simultaneously. Or alternatively, the sensitivity and reproducibility on quantitation by a multiple scanning of a single test on multi-analytes can be achieved. The detector of the scanning and analyzing apparatus of the present invention uses a fiber optical photodiode array to increase the signal-to-noise ratio, i.e., sensitivity, by cutting down the stray light noises and dark current from the light source.

Figure 4:
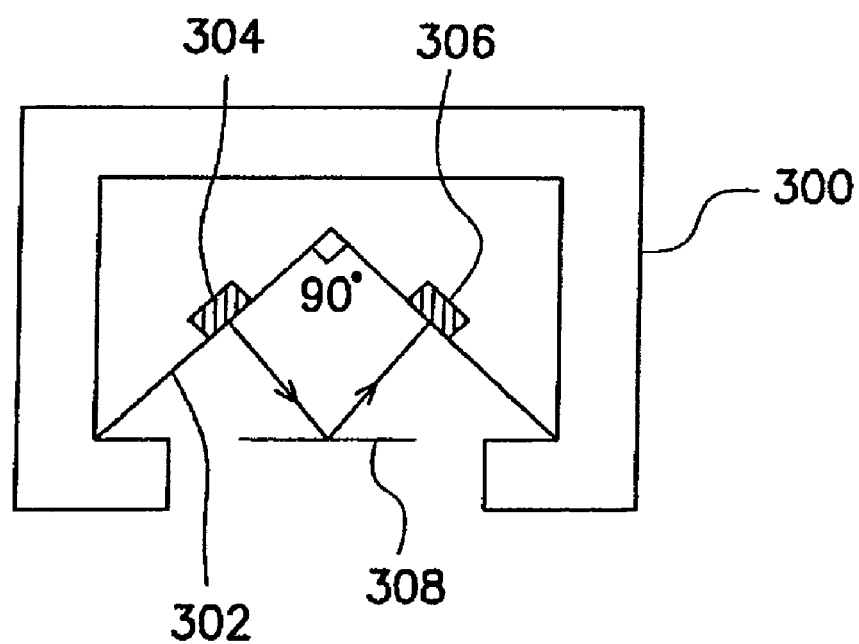
FIG. 4 is a cross-sectional view, schematically illustrating the scanning device in FIG. 1. according to an embodiment of the present invention.

In accordance to another aspect of the present invention, the LED array light source and the fiber optical photodiode array of the scanning and analyzing apparatus can be placed at 90 degree from each other in a reflectometric scanner case of current practice or 45 degree angle for fluorescent measurement in the certain application. As for example shown in FIG. 4. an integrated modular scanning probe 302 implemented on a step motor 300. The integrated modular scanning probe 302 includes an LED array 304 on one side of a case to serve as a light source and a photodiode detector array 306 on the other side of the case. As a result, the photodiode detector array 306 and the LED array 304 of the integrated modular scanning probe 302 has an including angle of, for example, 90 degrees. The test paper to be scanned is disposed on a paper tray 308 at the position to reflect the light from the LED array 304 to the photodiode detector array 306.

Figure 2:
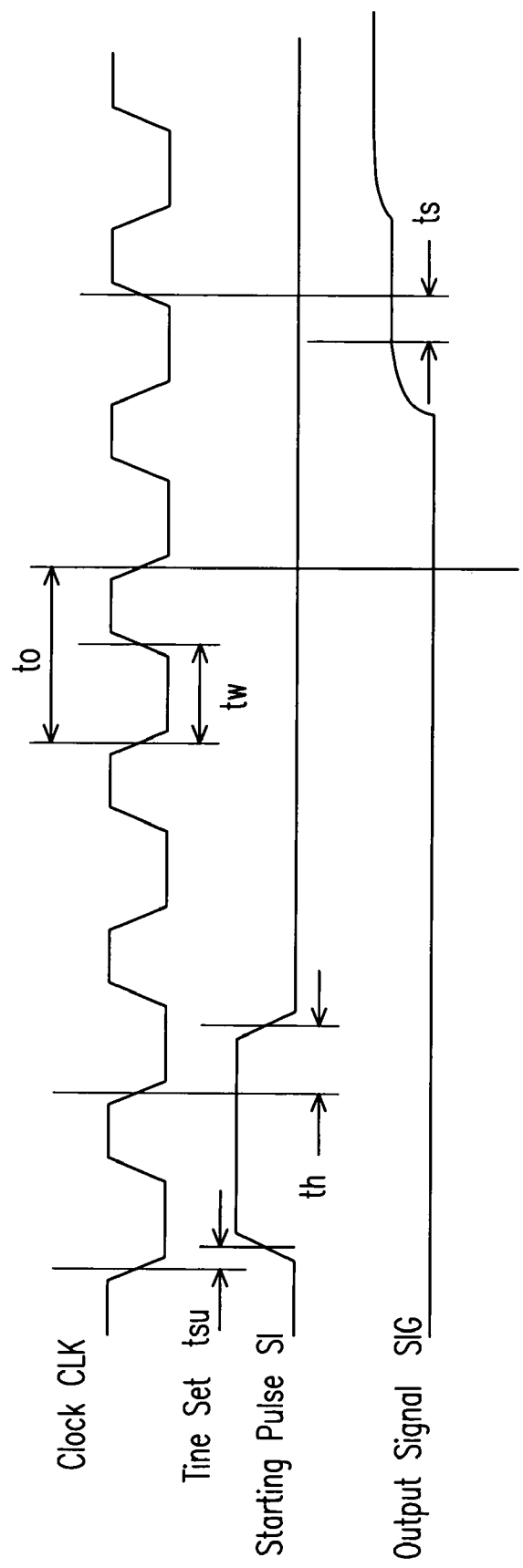
FIG. 2 is timing diagram of the above exemplary integrated probe of the portable, scanning and analyzing apparatus of the present invention.

FIG. 2 is timing diagram of the exemplary integrated probe. When the pulse is 1.0 MHz, the sampling time (ts) is reduced to about $10^{-9}$ second. Therefore, the resolution of the light source of the scanning and the analyzing apparatus of the present invention can reach to about 600 DPI and the light source array spans across 5.42 cm in width. Further, the photodiode detector used in the scanning and analyzing apparatus equipped with, for example, 1000 to 2000 pieces of optical fiber to sense the light reflect from sample surface and outputs a low dark current that requires only $10^{-9}$ second of the machine warm-up time and the sampling time. In one embodiment, the scanning and analyzing apparatus equipped with 1280 pieces of optical fiber.

Since the LED array light source and the optical fiber photodiode detectors of the scanning and analyzing apparatus of the present invention are arranged in an array, the possibility of affecting the entire operation due to the ineffectiveness of a few of the LED light sources or the photodiodes is mitigated. Therefore, the collection of signal by this optical unit is rather stable. The resolution of the integrated probe of the present invention can be as high as 600 PSI and the resolution is much higher than a customary probe.

It is appreciated that the application of the portable scanning analyzing apparatus introduced here is not restricted to the integrated probe with the aforementioned specifications. The scanning and analyzing apparatus can be modified, and other components can be introduced in accordance to the type of samples being tested, the test sites, the timing of the test and the analysis parameters.

Accordingly, having a LED array light source and an optical fiber photodiode array integrated as a scanning probe, the portable, scanning and analyzing apparatus can be miniaturized. Different styles of the apparatus can be provided for different situations and users, for example, the desk-top type, the touch-screen type and the handheld type.

The scanner device and the controller device are coupled by a driver which includes at least a chip or a central processing unit (CPU) with a driving program. After receiving a driver signal, the driver activates the scanning device via the software and the integrated probe of the scanning analyzing apparatus performs scanning for the 5.42 cm-wide test paper. Actually, due to the integrated scan probe of the scanning and analyzing apparatus, the LED array light source and the optical fiber photodiode detection device can scan row-by-row or column-by-column according to the setup of the scanner because both the light source and the detection device are configured in arrays. The scanning method can be modified to accommodate the test strip structures, the quantity of the test sample etc., for example, scanning block-by-block or region-by-region.

Since in the present invention, the reading of the test paper is conducted by scanning, the effective zone of test paper that can be used in analytical testing is greatly increased. Unlike in the prior art, only a restricted zone of the test strip is used for testing because reading of the test strip is directed to a fixed location of the test strip. Or, the reflect light of the whole test area is lumped together then the image is contracted or amplified to fit the charge couple device, CCD, i.e., the detector, by an optical system. The great resolution loss is usually experienced by either ways of the image processing. Therefore, by using the scanning analyzing apparatus of the instant invention, the effective zone of the test strip paper can be divided into regions according to the types of analyte that are going to be tested. For example, if a thin region of about 1-mm wide is sufficient for signal detection for one type analytes, the test strip is sufficient to carry many analytes for detection. It has being observed that the biological samples always introduce variable staining background along the direction of test strip paper development. A software algorithm is necessary to eliminate the floating baselines to enhance reproducibility especially when multi-analytes analysis is performed. Further, a single test with multiple scans is adequate for quantitatively analyzing the multi-analytes in the specimen. The scanner device of the present invention is activated by software. The integrated probe of the scanning and analyzing apparatus then conducts a line scan for the full width of the test paper. The rapid analyzing of the test samples by means of scanning greatly improves the efficiency and performance of sample analysis.

Further, the scanning and analyzing apparatus of the invention can include a step-in motor, for example. The step-in motor, which activated the rolling of the optical unit or the test strip paper through a step-in motor driving program stored in a chip or in the central processing unit of the driver device. The test strip paper is positioned at an appropriate scanning site in the scanning and analyzing apparatus, and the scanning of the test paper is conducted using the integrated scan probe of the scanning and analyzing apparatus.

It is recommended that the portable, scanning and analyzing apparatus is used in combination with a test paper designed with an antibody or antigen selective coloring technique such that the sensitivity and reproducibility of the analysis are increased. This technique applies a reactive dye to selectively dye protein or molecules by covalently bonding an antigen or an antibody with the reactive dye used in the textile industry. Details of such technique are disclosed in a series of patent applications for many countries and can be referred to ROC Patent no. 164331 and PRC Patent No. 146372.

The present invention can use the various dyeing techniques in combination with the light source of the scanning and analyzing apparatus to analyze different analytes, which can be dyed into various colors, including fluorescent dyes. The present invention is adaptable for clinical analysis of multi-analytes. By dyeing the different substances into different colors, multi-analytes in a test sample can be separated and analyzed by a single test with multiple scans on the full width of the test strip paper to accurately detect the different analytes that need to be determined.

In general, when a single color is used to dye all the antibodies and if the concentration differences of the analytes to be tested in one test specimen is greater than $10^6$ times, it may not be possible to detect all the analyzes in one batch of analysis. Since, if the sensitivity of the scanning and analyzing apparatus is adjusted to detect for the low concentration analyte, the concentration changes in the high concentration analyte may not be easily detected, and vice versa. The portable, scanning and analyzing apparatus of the present invention is therefore suitable to test specimens with multi-analytes of large concentration differences. If the aforementioned reactive dye is used to selectively dye analyte, the scanning and analyzing apparatus can maintain a sufficient sensitivity to different types of analytes. In accordance to the present invention, in combination with the aforementioned dyeing techniques being applied to the test strip paper, only single test is sufficient to analyze a test sample with multi-analytes of high concentration difference. Further, the linear range for quantification is broader. The quantitative result is thus more reliable so that the customary problems encountered in the prior art devices are resolved.

For example, the concentration of the C-reactive protein, CRP, in the blood sample of a urocystitis, a prostate cancer or a prostatomegaly patient is in the order of mg/ml, while the concentration of the total prostate specific antigen, t-PSA, is in the order of $10^{-9}$ g/ml(nanogram/ml). The concentration difference is about $10^6$ times. FIGS. 3a & b are the calibration curves of the diseases markers for prostate cancer screening i.e., prostate specific antigen-total and C-reactive protein, CRP, measured by portable, scanning and analyzing apparatus. Since the CRP concentration in the test sample is very high, if using the colloid gold to dye the t-PSA antigen into a magenta color, the magenta color developed for CRP is very dark. The multiple detections of the color changes in CRP together with t-PSA on one test paper are thereby difficult. While the same color for labeling antibodies the color development for the extremely high and low concentration analytes is insufficient to cover both for detection. However, if the CRP is colored with a dye which is less sensitive to the light source, and the t-PSA dyed with colloid gold, the concentrations of CRP and t-PSA can be quantified in a single test operation with multiple scans. The point-of-care testing can be provided and the appropriate therapeutic attention can be given to the patient immediately.

Further, since the effective scan area of the present invention is broader, ten or even more analytes if necessary, for example, in a single test specimens can be simultaneously scanned (for example, the detection of various indicators in hepatitis B infection on one test paper) and quantitated.

Compared to the prior art, both the light source and the detection device of the scanning and analyzing apparatus of the present invention are arranged integrally in an array as the optical unit in scanner device 110. Not only the instrumentation size is reduced to compact and light weight, the warm-up and sampling times are shorter. Therefore, the signals are more stable than a device where the light source and the detection device are not configured integrally in an array. And it shall be more suitable to be utilized in many POCT sectors than the prior arts.

Compared to prior art, the computing algorithm treating floating baselines among the optical signals of multi-analytes can greatly reduce the noises and generate high S/N test signals of this scanning and analyzing apparatus, whereas, the instruments equipped with CCD detectors are failed to compensate.

Compared to the prior art, the detector of optical unit of the scanning and analyzing apparatus consists of fiber optics element which helps the system not only to eliminate the dark current from thermal noise but also minimize the stray light irradiation from LED light source, both of which successfully enhance test signal S/N, in the absence of elaborate monochromatic system in the sophisticate instrumentations and contribute to size reduction of the scanning and analyzing apparatus.

Compared to prior art, the portable, scanning and analyzing apparatus utilizes an efficient, miniature step-in motor in its scanner device 110 when it received order from driver signal 14 to the driver device 130 according to the control signal 12 from computing unit 170, the motor is activated and proceeds scanning consecutively. The optical signals are individually processed and summing up to statistically attain sensitivities, whereas, no prior art has found to get this process involved.

Owing to the unevenly porous nature of the test paper, single reading would hardly obtain an accurate result. Compared to prior art, rarely the analytical systems have utilized an algorithm to operate the repeated scanning of the test strip paper for statistically improving reproducibility. In the scanning and analyzing apparatus, system impression could be reduced from ~20% to 7~10% accordingly after the algorithm was undertaken.

The portable, scanning and analyzing apparatus of the present invention provides many thus mentioned improvements to the various drawbacks of the conventional approach in sample detection and analysis. The portable, scanning and analyzing apparatus allows assay to be more simple, convenient and reliable, etc., which is appropriate to use in intensive care units, home cares, emergency rooms, clinics, ambulances, drug screening and even farming application, . . . etc. After a specimen to be tested is withdrawn from a patient and is reacted in the test paper, an analytical result is obtained almost immediately subsequent to placing the test paper in the apparatus of the present invention. Thus, a prompt intervention of the illness can be provided to the patient. Especially for certain contagious diseases and for cardiac-vascular diseases the rapid turn-around-time for the analytical results is prevalent to a timely administration of the appropriate care to the patient in order to prevent a further deterioration of the illness. In drug screening, the portable, scanning and analyzing apparatus of the invention can perform the analysis to attain immediate quantitative results on-site, which favorably reduces the potential problems on the preservation and contamination of the test samples.

The apparatus of the present invention is applicable for the testing of prostate cancer, myocardial infarction, Kawasaki disease, drug of abuse, and for an on-site detection of drugs and illegal prescriptions. The apparatus of the present invention is also applicable for the separation and the detection of types of hepatitis, monitoring of the medication, detection of venereal disease and pregnancy.

In accordance to the present invention, the portable, scanning and analyzing apparatus is sufficiently compact therefore, it can be portable to use in various situations and to provide the timely medical treatment.

Further, the apparatus of the present invention provides an on-site detection and an immediate analytical result by a computing unit of the apparatus to give an accurate and objective diagnosis.

Moreover, the present invention can apply the appropriate test strip paper for quantitative analysis. Not only the analysis procedure is simple, immunoanalysis and other color display reaction tests are facilitated.

However, the portable, scanning and analyzing apparatus of the present invention is not limited to in conjunction with aforementioned dying technique. As a matter of fact, directing to different types of test sample, different testing situation and condition, and analytical parameters, the present invention is compatible with other conventional or easily anticipated methods or mechanisms on modifying the color display properties of the test strip paper or on enhancing the detection quality.

It will be apparent of those skilled in the art that various modifications and variations can be made to the structure of the present invention without departing from the scope or spirit of the invention. In view of the forgoing, it is intended that the present invention cover modifications and variations of this invention provided they fall within the scope of the following claims and their equivalents.

What is claimed is:

1. A portable, scanning and analyzing apparatus, used to scan a test paper and the test paper comprises a test sample thereon, the scanning and analyzing apparatus comprising:

a scanner device, for scanning the test paper and outputting a test signal corresponding to the test sample, wherein the scanner device comprises an integrated modular scanning probe comprising at least a light emitting diode (LED) array light source and at least a photodiode detector array assembled together in the integrated modular scanning probe, wherein the LED array light source emits a light to the test paper and the test paper reflects the light to the photodiode detector array, wherein the light from the LED array light source is incident to a surface of the test paper by an incident angle of 45 degrees from a normal direction of the surface of the test pate and the test paper reflects the incident light by deflecting 90 degrees from the incident angle;

a computing unit, coupled to the scanner device to receive and analyze the test signal, wherein the computing unit receives an incoming command and accordingly outputs a control signal;

a controller, coupled to the computing unit, wherein the controller outputs a driver signal in accordance with the control signal received; and a driver device, coupled with the controller device and the scanner device, wherein the driver device receives the control signal and accordingly drives the scanner device to scan the test paper.

2. The scanning and analyzing apparatus of claim 1, wherein the scanner device comprises of an optical unit integrated from the LED array light source and the photodiode detector array, a step-in motor and a test paper tray for holding the test paper.

3. The scanning and analyzing apparatus of claim 2, wherein the computing unit is used to at least perform an optical signals' floating baselines management, a test signal summing up manipulation and a driven mechanism to move the optical unit repeatedly over the test paper.

4. The scanning and analyzing apparatus of claim 1, further comprising a signal amplifier that is coupled with the scanner device to amplify the test signal.

5. The scanning and analyzing apparatus of claim 3, further comprising an analog/digital converter that is coupled with the signal amplifier to receive the amplified test signal, wherein the analog/digital converter converts the amplified test signal into a digital signal that is transferred to the computing unit.

6. The scanning and analyzing apparatus of claim 1, further comprising a serial interface that is placed between the computing unit and the controller device to enable the control signal transferring between the computing unit and the controller device.

7. The scanning and analyzing apparatus of claim 6, wherein the interface is a standard RS-232 interface.

8. The scanning and analyzing apparatus of claim 1, wherein the test sample comprises a blood sample.

9. The scanning and analyzing apparatus of claim 1, wherein the test sample comprises a body fluid.

10. A scanning and analyzing apparatus for scanning a test paper and a test sample thereon, the scanning and analyzing apparatus comprising:

a scanner device that scans the test paper and outputs a test signal in accordance with a test result of the testing sample, wherein the scanner device comprises an integrated scan probe that comprises at least one light emitting diode (LED) array light source and at least one photodiode detector array assembled together in the integrated scanning probe, wherein the LED array light source emits a light to the test paper and the test paper reflects the light to the photodiode detector array, wherein the light from the LED array light source is incident to a surface of the test paper by an incident angle of 45 degrees from a normal direction of the surface of the test pate and the test paper reflects the incident light by deflecting 90 degrees from the incident angle;

a signal amplifier that is coupled with the scanner device, wherein the signal amplifier receives, amplifies and then outputs the test signal;

an analog/digital converter that is coupled with the signal amplifier, wherein the analog/digital converter converts the amplified test signal into a digital signal and outputs the digital signal;

a computing unit that is coupled with the analog/digital converter, wherein the computing unit receives and processes the digital signal, and outputs a control signal after receiving a command;

a controller device that is coupled with the computing unit, wherein the controller device receives the control signal and accordingly outputs a driver signal;

an interface that is placed between the computing unit and the controller device, wherein the interface enables the control signal transferring between the computing unit and the controller device; and a driver device that is coupled with the controller device and the scanner device, wherein the driver device drives the scanner device to scan the test paper in accordance with the driver signal.

11. The scanning and analyzing apparatus of claim 10, wherein the interface is a standard RS-232 interface.

12. The scanning and analyzing apparatus of claim 10, wherein the test sample comprises a blood sample.

13. The scanning and analyzing apparatus of claim 10, wherein the test sample comprises a body fluid.

14. The scanning and analyzing apparatus of claim 10, wherein the scanner device comprises an optical unit integrated from the LED array light source and the photodiode detector array, a step-in motor and a test paper tray for hold the test paper.

15. The scanning and analyzing apparatus of claim 14, wherein the computing unit is used to at least perform an optical signals' floating baselines management, a test signal summing up manipulation and a driven mechanism to move an optical unit repeatedly over the test paper.

* * * * *